US012044635B2

(12) United States Patent
Kent et al.

(10) Patent No.: US 12,044,635 B2
(45) Date of Patent: Jul. 23, 2024

(54) MATERIALS CLASSIFIER

(71) Applicant: BAE SYSTEMS plc, London (GB)

(72) Inventors: Lionel William John Kent, Chelmsford (GB); Jason John Lepley, Chelmsford (GB)

(73) Assignee: BAE SYSTEMS PLC, London (GB)

( * ) Notice: Subject to any disclaimer, the term of this patent is extended or adjusted under 35 U.S.C. 154(b) by 279 days.

(21) Appl. No.: 17/753,016

(22) PCT Filed: Aug. 13, 2020

(86) PCT No.: PCT/GB2020/051927
§ 371 (c)(1),
(2) Date: Feb. 15, 2022

(87) PCT Pub. No.: WO2021/032951
PCT Pub. Date: Feb. 25, 2021

(65) Prior Publication Data
US 2022/0334071 A1    Oct. 20, 2022

(30) Foreign Application Priority Data
Aug. 21, 2019   (GB) ...................................... 1911991

(51) Int. Cl.
*G01N 23/20066*    (2018.01)
*G01N 33/22*    (2006.01)
*G01V 5/222*    (2024.01)

(52) U.S. Cl.
CPC ..... *G01N 23/20066* (2013.01); *G01N 33/227* (2013.01); *G01V 5/222* (2024.01); *G01N 2223/053* (2013.01)

(58) Field of Classification Search
None
See application file for complete search history.

(56) References Cited

U.S. PATENT DOCUMENTS 5,557,108 A * 9/1996 Tumer .................. G01V 5/223
                                                                250/391
5,600,303 A    2/1997 Husseiny et al.
(Continued)

FOREIGN PATENT DOCUMENTS

EP           3528012 A1    8/2019
WO     2010070327 A1    6/2010
(Continued)

OTHER PUBLICATIONS

International Preliminary Report on Patentability received for PCT Application No. PCT/GB2020/051927. Mail date: Mar. 3, 2022. 10 pages.
(Continued)

*Primary Examiner* — Hoon K Song
(74) *Attorney, Agent, or Firm* — Finch & Maloney PLLC

(57) ABSTRACT

A method and apparatus for classifying and/or identifying materials by means of their spectral response to gamma radiation. Classification is carried out by irradiating multiple different samples with gamma radiation, detecting a spectral response in the backscatter direction, sorting the spectral response into energy bands and selecting a combination of energy bands to define a relationship that best distinguishes between clusters of spectral responses for different material classes. Two or more of the energy bands may overlap.

20 Claims, 9 Drawing Sheets

(56) References Cited

U.S. PATENT DOCUMENTS

2012/0201356 A1* 8/2012 Rothschild .......... G01N 23/203
378/87
2019/0129060 A1 5/2019 Arodzero et al.

FOREIGN PATENT DOCUMENTS

WO 2011110863 A1 9/2011
WO 2021032951 A1 2/2021

OTHER PUBLICATIONS

International Search Report and Written Opinion received for PCT Application No. PCT/GB2020/051927. Mail date: Dec. 1, 2020. 15 pages.
GB Search Report under Section 17(5) received for GB Application No. 1911991.6, dated Jan. 29, 2020. 3 pages.

* cited by examiner

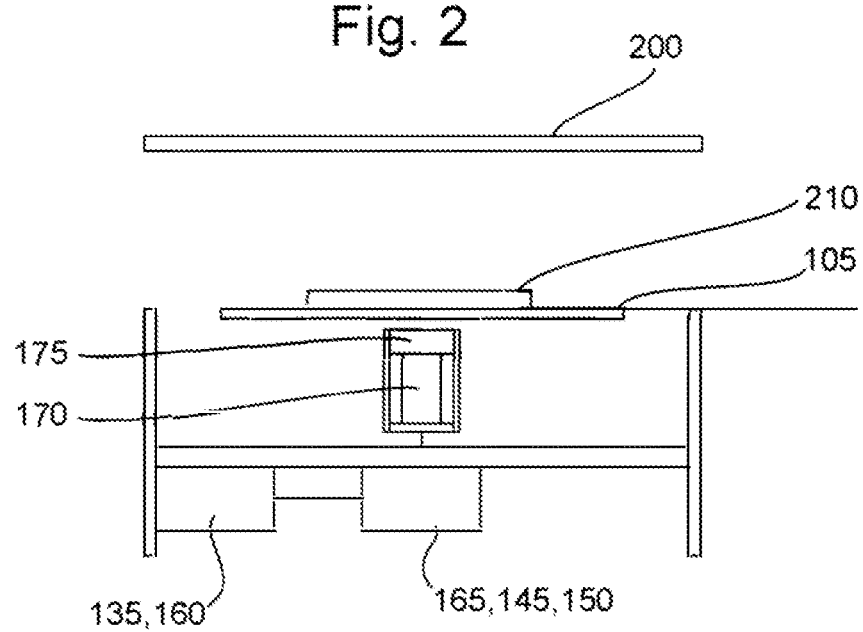
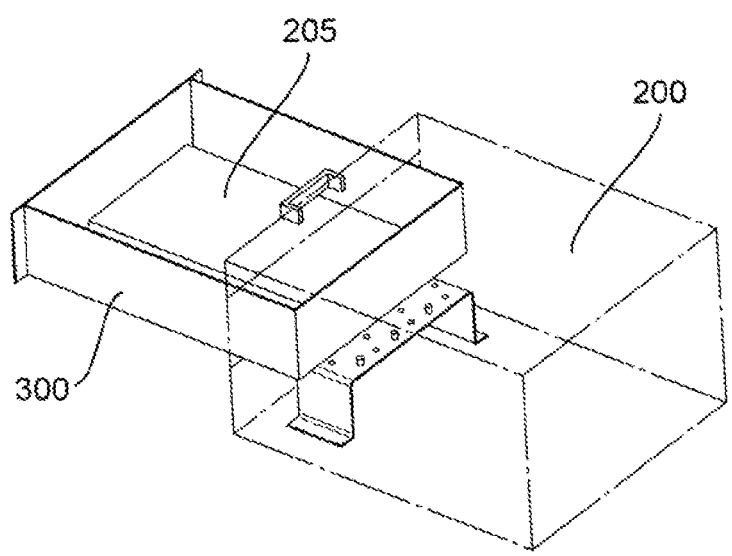

MATERIALS CLASSIFIER

The present invention relates to a materials classifier based on gamma spectroscopy. It finds application in distinguishing explosive materials from non-explosive materials but can be used for the detection of other target materials such as drugs.

Various materials such as explosives, illegal drugs, contraband metals and other materials may be concealed for various reasons. The proliferation of portable electrical devices represents an improved opportunity for terrorists to smuggle explosive devices.

It is known to use for example X-rays, metal detectors and millimetre wave devices to interrogate people and objects, such as luggage. However, the known techniques suffer from various drawbacks and generally can provide only crude results. Existing solutions fall generally into two categories:
- security screening situations in which known solutions are unable to detect and distinguish drugs and explosives from other materials, and are primarily concerned with the detection of weapons.
- solutions developed specifically to detect and recognise drugs and explosives. These generally require there to be trace quantities of the explosive in direct contact with the sensor. They are unable to detect and recognise hermetically, or well-sealed, materials.

According to a first aspect of the present invention, there is provided a materials classifier for use in detecting the presence of at least one material or material type in a sample or object under test, the detection system comprising:

a gamma radiation source holder for holding two or more gamma radiation sources for irradiating a sample test location;

a detector for detecting radiation events in a backscatter direction from the test location, the events lying in at least three different detected energy bands; and a classifying analyser for analyzing two or more relationships between detected radiation events in the at least three different detected energy bands, the analysis being carried out for at least two different materials or material types, the classifying analyser being configured to select a preferred relationship for distinguishing between the at least two different materials or material types.

The gamma radiation source holder may comprise at least two different holder constructions that in use hold sources for generating radiation in at least two different respective source energy bands. Alternatively, each holder construction may be designed to hold a mixed source comprising more than one gamma radiation emitting material.

The classifying analyser might for example compare values for detected events lying in respective ones of the at least three energy bands. The values may comprise the number of detected events lying in the respective energy bands.

The classifying analyser may include a multidimensional plotter for plotting relationships between detected events for different materials or material types, in relation to axes which each represent values arising in a respective energy band. The classifying analyser may then select a preferred relationship for distinguishing between the at least two different materials or material types. The preferred relationship will usually be a relationship that generates the most distinguishable clusters of results for the different materials or material types.

Embodiments of the invention provide apparatus and a method for extracting multi-spectral data from the spectral response signatures of different materials or material types, and applying the extracted data in improved distinction of two or more materials or material categories by means of their composition.

Notably, the at least three different detected energy bands on which relationships are based are not necessarily mutually exclusive. Thus two or more of these detected energy bands may show spectral overlap. To support this, the detector may be configured to provide a sorted, or channelized, output to the classifying analyser, each sort category or channel relating to detected energy events in a respective detected energy band, the analyser being configured to combine output from more than one category or channel to generate data for plotting a relationship. Where two or more of the detected energy bands on which a relationship is based show spectral overlap, the output from at least one category or channel will be used to generate data for plotting in relation to more than one detected energy band.

An event may comprise a pulse output produced by the detector in response to detected radiation.

A materials classifier according to an embodiment of the present invention will now be described by way of example only with reference to the accompanying schematic drawings of which:

FIG. 2 shows a side elevation of test apparatus for use in the assembly of FIG. 1;

FIG. 3 shows a quarter view from above of a drawer arrangement for positioning a sample to be tested using the assembly of FIG. 1;

Embodiments of the invention use the principle of detected energy received from target materials of different chemical composition when exposed to one or more gamma radiation emission source types. The materials respond by producing photons to give characteristic emission spectra. Each radiation source will have a characteristic emission spectrum characterising the energy (or, equivalently, frequency) of the emitted photons.

In accordance with the Compton scattering theory, retro-scattered photons (i.e. photons scattered along the same axis as, but in the opposite direction to, the incident photon) will have an energy lower than the incident photon, where the energy difference results from an inelastic energy exchange between the incident photon and a recoil electron in the target material.

Additionally, materials may fluoresce in response to the incident gamma radiation. This occurs when the energy of incident radiation is greater than the binding energy of inner shell electrons in the target material. If this is the case, then the target material can produce X-ray fluorescence.

Equipment that would be suitable for use in embodiments of the present invention is disclosed in co-pending patent applications of the applicant as follows:
EP 3528012 which discloses a radiation backscatter detector having a tessellated array of scintillator detectors;
EP 18275149.5 which discloses a source array mounting scheme; and
EP 19154080.6 which discloses a calibration technique for a scintillator detector.

Figure 1:
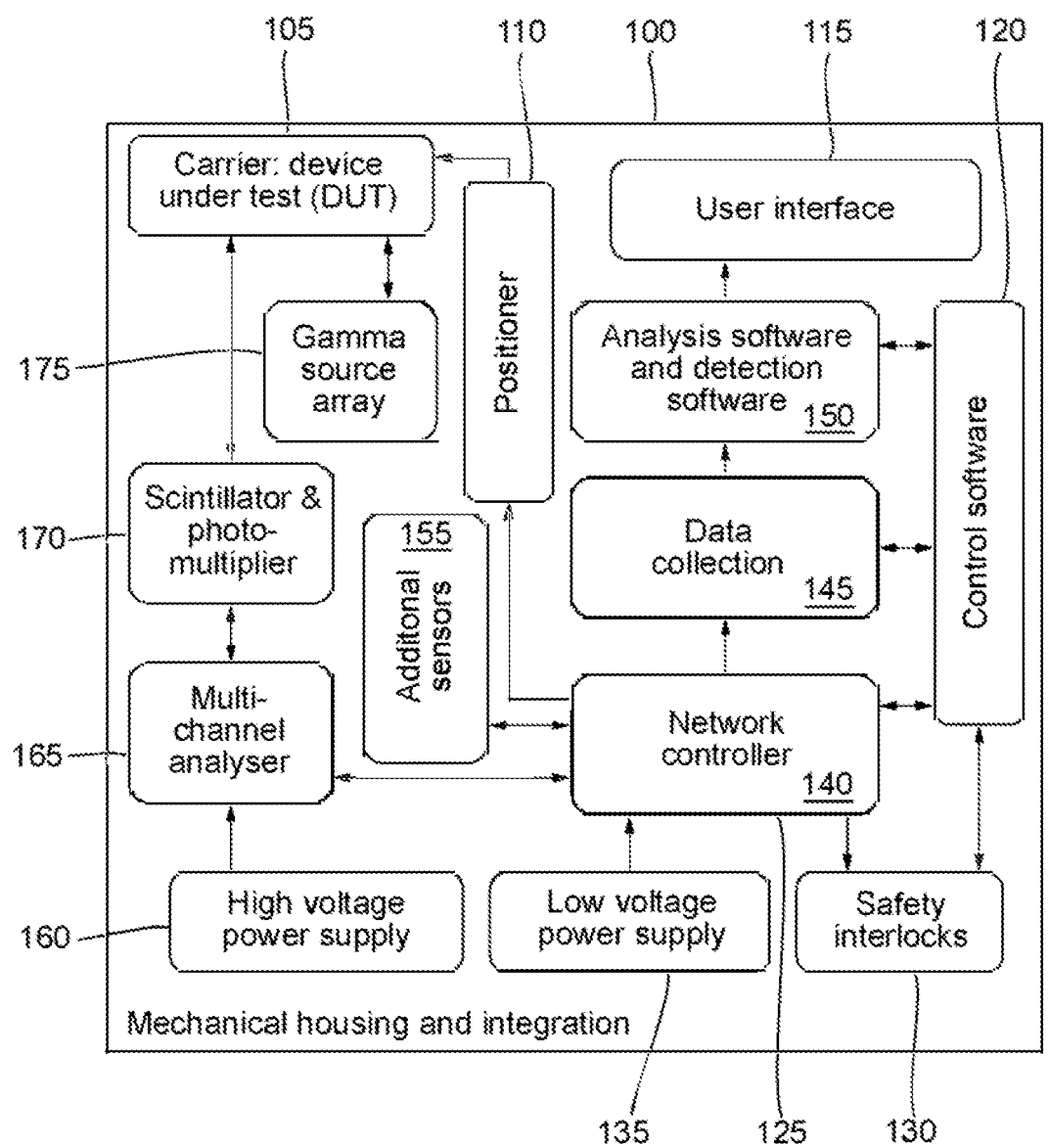
FIG. 1 shows a diagram of components of the detector assembly.

Referring to FIG. 1, the detector assembly 100 is based on a carrier 105 for a device under test (DUT), located where it can be irradiated by a source array 175 and where emitted photons can be picked up by a detector 170. Either the source 175 or the carrier 105 might be mobile for scanning purposes. As shown in the embodiment of FIG. 1, the carrier 105 is mobile, having a positioner 110 for actuation and sensing to control the 2D positioning of the DUT. The carrier comprises for example an X-Y stage carrier 105.

A multichannel analyser 165 receives output from the detector 170 which is delivered to a data collector 145 and analysis software 150 via a network controller 140. The network controller 140 has a coordinating and generally controlling role in relation to use of the assembly 100. For instance, it implements commands received via a user interface 115, moves the positioner 110 and coordinates the data received via the multichannel analyser 165.

The assembly also has low and high voltage power supplies 135, 160 of known type for the electronic and mechanical components and suitable safety interlocks 130 to protect the user in view of the source array 175. The high voltage supply supplies line voltages greater than 48V. High voltages are input to the unit as mains supply before conversion to low voltage levels. The low voltage supply connects external power to provide low voltage power for the system elements. The safety interlocks 130 are connected to points of user access to the DUT carrier 105. These prevent access during operation.

Referring to FIG. 2, the physical relationship between main components of the assembly 100 will generally be an X-Y stage platform 105 for a DUT 210, positioned above a source array 175 with detector 170 below it. The device under test 210 might be for example a laptop or tablet. A data collection and analysis channel 165, 145, 150 receives the output of the detector 170 and the low and high voltage power supplies 135, 160 are supported near the movable carrier 105 and the electronic components. Shielding 200 protects the user from any residual stray radiation.

Referring to FIG. 3, an alternative example of a carrier 105 for a DUT 210 is a tray enclosure mechanism. This is advantageous in protecting a user from the source array 175 as the DUT 210 is placed into position for irradiation. In this case, it is the source array 175 which will be moved by the positioner 110 to achieve scanning, once the carrier 105 has been pushed home into a shielded enclosure 200. The purpose of the enclosure 200 is both to isolate the DUT during a scan and to protect the safety of the operator from potential exposure to the sources. The outer shape and dimensions can be designed to physically prevent anyone from exposing themselves to the radiation. This can be achieved through a combination of range and shielding material; the former being maximised within the size requirements to minimise the latter (which impacts the weight.)

Figure 4:
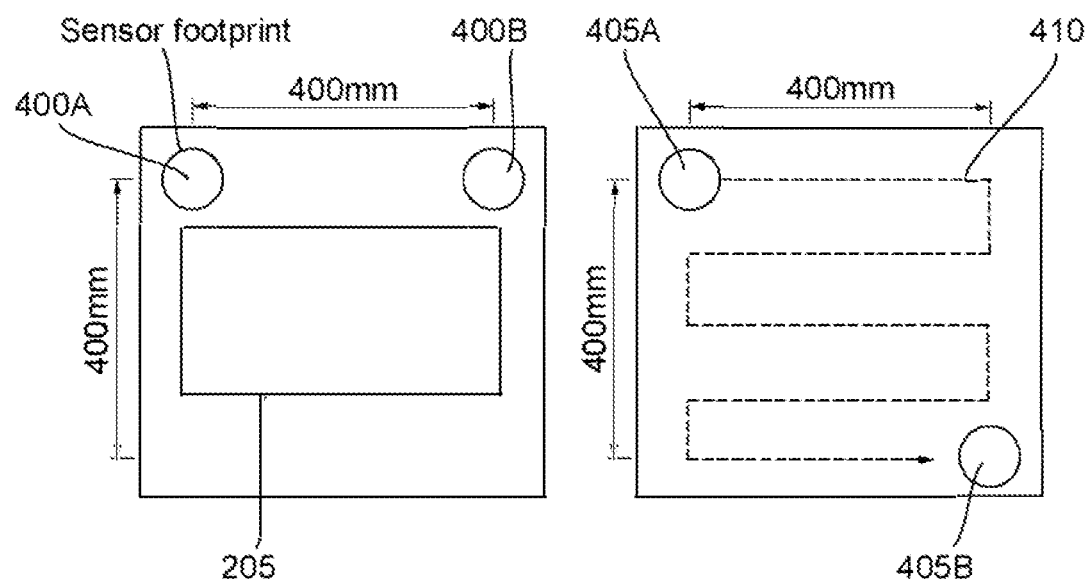
FIGS. 4 and 5 show alternative scanning regimes for use in the assembly of FIG. 1.
Figure 5:
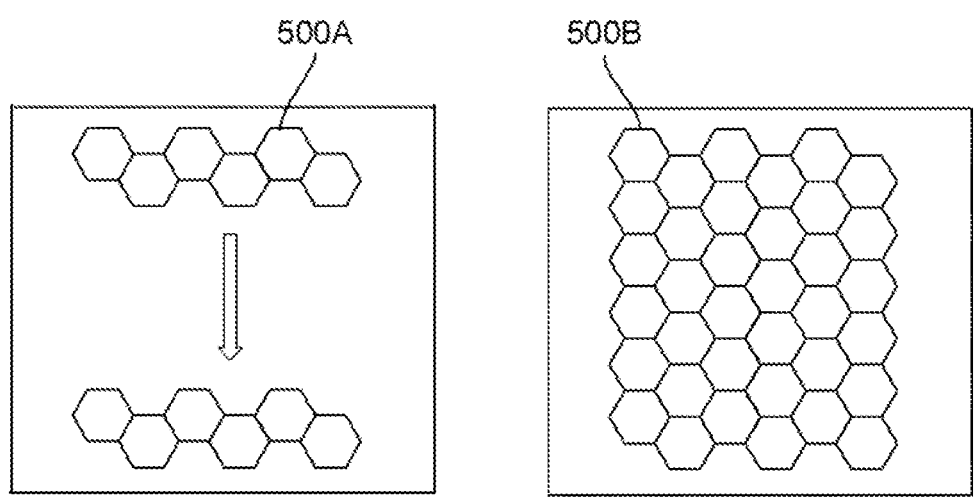

Referring to FIGS. 4 and 5, a source array 175 having a footprint 400 in relation to a carrier 205 may be scanned within positioning limits 400A, 400B along two orthogonal axes to follow a raster scanning pattern 410. Alternatively, the source array 175 might be configured as a linear array 500A which is scanned in one direction only, or as a full two-dimensional grid 500B which removes the need for either a moving carrier 205 for the DUT 210 or a moving source array 175.

Figure 6:
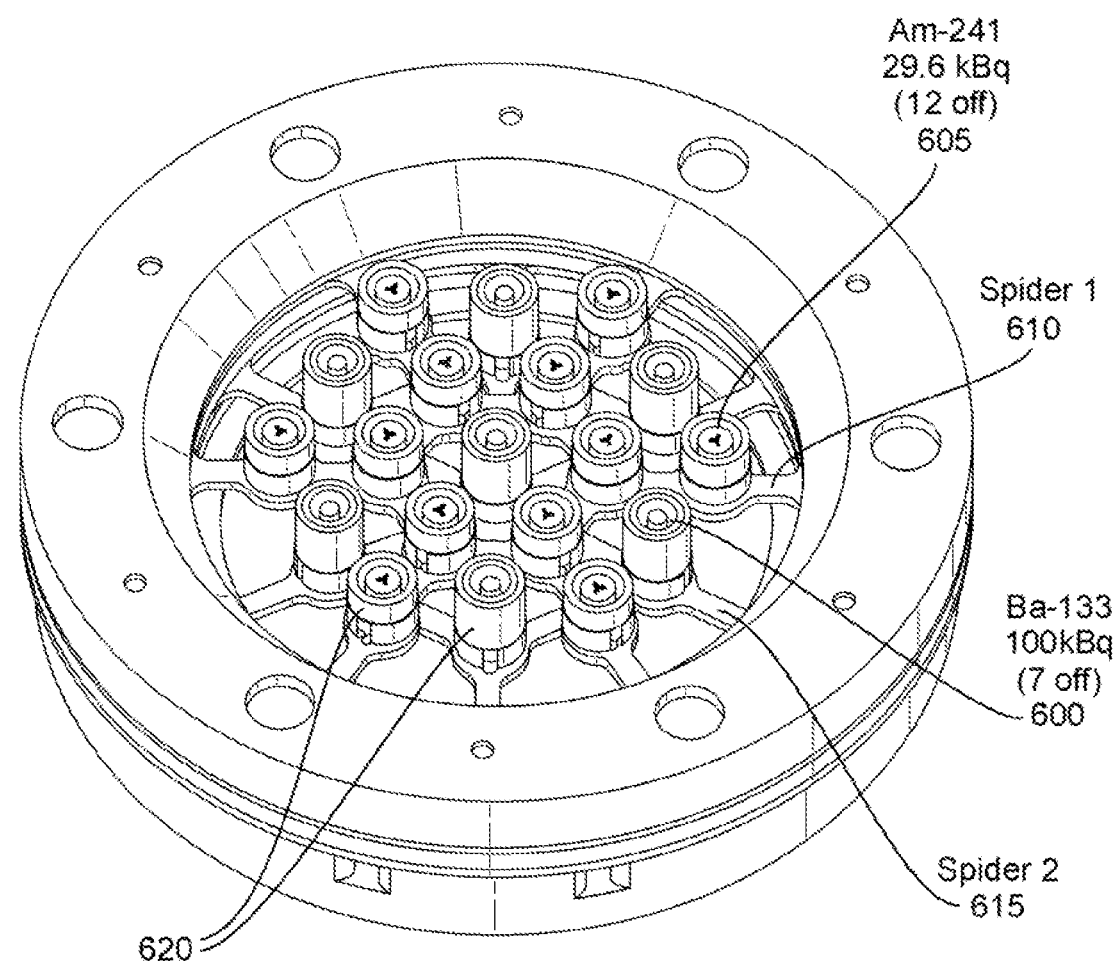
FIG. 6 shows a quarter view from above of a source array configuration for use in the assembly of FIG. 1.
Figure 7:
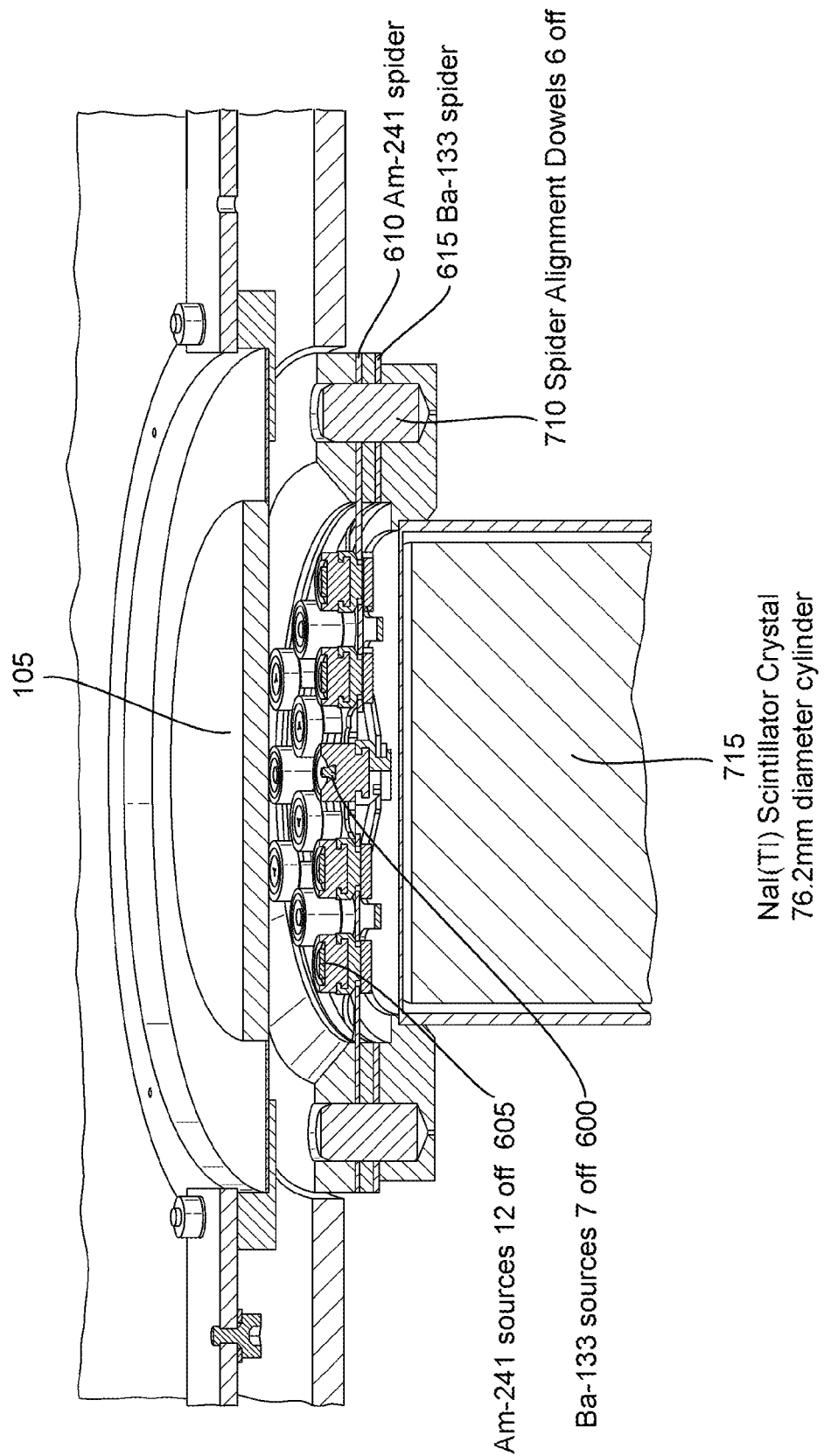
FIG. 7 shows a cross section through the source array configuration of FIG. 6, supported in relation to a location for a device under test and a scintillator crystal, as might be used in the assembly of FIG. 1.

Referring to FIGS. 6 and 7, a gamma source array is shown and described in order to show the general principles of an array. Preferably for the purposes of the present invention, at least one of the radio-isotope sources needs to have an energy of greater than the binding energy of the inner shell electrons of a material under test.

A source array for detecting radiation energies in a backscattered direction in general might comprise seven barium (Ba-133) sources 600 and twelve americium (Am-241) 605. The gamma sources are evenly distributed. The Am-241 sources 605 are mounted in shorter lead shields than the Ba-133 sources 600. This overall configuration of multiple sources reduces the rate at which the resultant gamma flux falls with distance r from the source plane. By comparison, the gamma flux of a single point source decreases at a rate of approximately $1/r^2$.

A feature of the source array design is a modular approach that allows different combinations to be created readily. This was achieved by using aluminium spiders 610, 615 to mount each of the source types, aligned with dowels 710. A first spider 610 carries the twelve Am-241 sources 605 of activity 29.6 kBq each in two separate rings of six. This spider 610 has 6-fold rotational symmetry. A second spider 615 carries the seven Ba-133 sources 600 of activity 100 kBq each in an outer ring of six sources with one source on the centre axis. This spider 615 again has sixfold rotation symmetry.

The sources 600, 605 are placed in recesses in lead shields 620 and are then held captive in place by 50 μm thick aluminium covers bonded onto the lead shield 620 using an epoxy resin. A small air bleed hole is included in the aluminium cover. This in operational use would provide pressure equalisation when the system was airborne at lower than sea level atmospheric cabin pressure.

The lead shielded sources are then mounted on a 1 mm thick aluminium spider 610, 615 using a pair of brass, or preferably tungsten copper alloy, claws. A lip in the claw engages with an annular groove in the cylindrical surface of the lead shield 620 to hold it captive. The claws for their part are held captive with the aid of 3D printed 'Euro' clips made from Photopolymer resin (FLTOTL03) supplied by GoPrint3D.

The outer diameter of all of the lead shields 620 is 10 mm.

The overall height of the lead shields used for the Am-241 sources is 6.2 mm. The thickness of the lead shield directly below the Am-241 sources is 4.8 mm. The thickness of the circular side wall of lead that holds the Am-241 captive sideways is 1.7 mm. The nominal mass of each of these lead shields is 3.72 grams.

The overall height of the Ba-133 lead shields was 10.2 mm, with ~7 mm of lead directly below each Ba-133 source. This was sufficient to stop virtually all transmission of the 81 keV and 31 keV emission lines of Barium-133. The side walls of these lead shields were 3.4 mm thick. This was sufficient to stop ~99.9% of incident 150 keV gamma from passing through. The nominal mass of each of these lead shields is 7.3 grams.

Notably, the 7 mm thick lead base of the shields was insufficient to stop the harder 302.9 keV, 356 keV and 383 keV emission lines of Barium-133. High energy gamma emission lines to varying degrees pass through the lead shield; albeit with a significant number of the original gamma photons subject to some small forward Compton scattering energy losses. So for example only ~74.8% of the incident 356 keV emission line photons line of Barium-133 will be full absorbed by a 7 mm thick layer of lead.

Additional radio-isotope sources that might be added to the source array to provide additional gamma lines include for example Cs-137 which generates a hard gamma at 661.7 keV. This particular gamma would produce a backscatter peak that would be distinguishable from the backscatter peaks generated by the Ba-133 and Am-241 sources mentioned above.

The array of sources is housed directly over a cylindrical thallium doped sodium iodide scintillator detector 715. Each of the sources 600, 605 is housed in a lead shield 620 to prevent direct transmission of gamma radiation from the sources to the scintillator detector 715 for energies less than ~160 keV. The spiders 610, 615 are designed so that the separation of the centre axis of any of the closest adjacent sources 600, 605 across the entire face of the scintillator aperture is 16 mm.

Various other mounting spiders and arrangements of sources might be used and can be combined to yield a variety of source array combinations. For example, it is possible to use a source array in which each source contains an appropriate mix of sources, for example Am-241 and Ba-133. This could allow reduction of the total number of lead shielded sources and so reduce the level of partial obscuration of the backscattered gamma from the target. Further, in a source array geometry in which seven 100 kBq sources and twelve 29.6 kBq Am-241 sources are provided separately, two backscatter features arise at respectively ~50 keV and ~60 keV due to respectively the 59.54 keV line of Am-241 and the 81 keV line of Ba-133, but the backscattered Am-241 feature is about half the activity of the backscattered Ba-133. In a source array in which each source contains an appropriate mix of sources, the strength of the backscattered Am-241 emission line could be approximately equal to that of the backscattered Ba-133 emission line.

Suitable Am-241 sources are supplied for example by High Tech Sources Limited (part number AMMK7650) and Ba-133 are supplied for example by Ritverc GmbH (part number GBa3.11).

A voltage setting for the detector 715 needs to be chosen to provide optimal spectral resolution over the energy range ~10 keV to 400 keV with no signal saturation, for example a high voltage setting of 960 volts might be found appropriate.

In use, backscattered and fluorescence radiation is collected by the scintillator detector 715 from which an energy spectrum can then be generated. A stored background spectrum due to the source array alone is subtracted to yield a background-corrected energy spectrum for a DUT 210.

Figure 8:
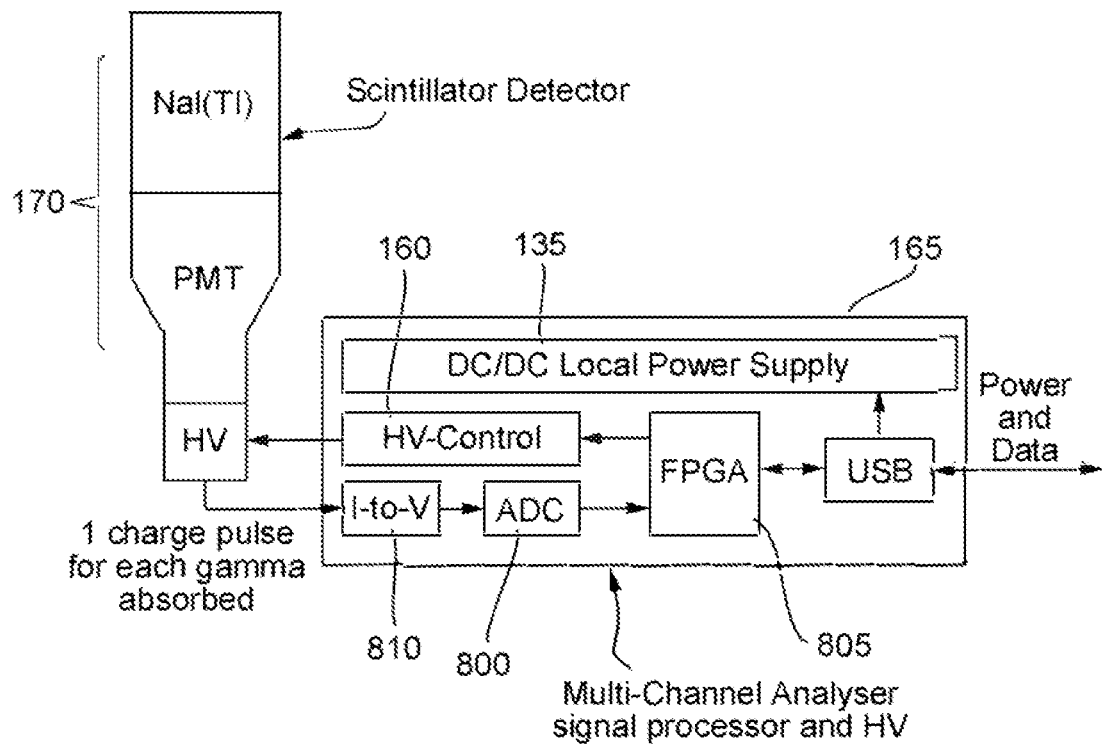
FIG. 8 shows a functional block diagram of detection equipment for use in the detector assembly of FIG. 1.

Referring to FIGS. 1 and 8, a functional block diagram for the gamma spectrometer's detector 165, 170 is as follows. The detector in this embodiment might be provided by a Saint Gobain model SGC-3M/3 scintillator detector 170, connected to multi-channel analyser 165 (MCA) such as a Bridgeport Inc. model SGC-600-7889.

The amplified electric charge from the photomultiplier is channelised by the MCA which has an "I-to-V" converter 810 for converting the incoming charge pulse into a voltage which is read by an analogue to digital converter (ADC) 800 that operates at a clock rate of 120 MHz. A field programmable gate array 805 (FPGA) samples the digital output from the ADC 800 to determine a total area of the voltage pulse profile. The FPGA 805 then assigns this area result to a digital channel whose value is linearly proportional to the original gamma photon energy.

The digitised data collected by the FPGA 805 is output via a USB controller 140 to software 145, 150, 120 run on a desktop computer that controls the overall detector system. For example, data can be analysed and displayed by control software such as 'eMorpho MCA Client'. The spectral data, the operating conditions and control parameter setting of the detector 170 can be saved to the hard drive as an .xml file.

Summing the backscatter counts from a DUT 210 over a time interval allows a backscatter energy spectrum of the target to be created. Initially the data would support a plot of counts versus energy channel number. More usefully, the data can be processed to support plots of counts versus energy band.

Figure 9:
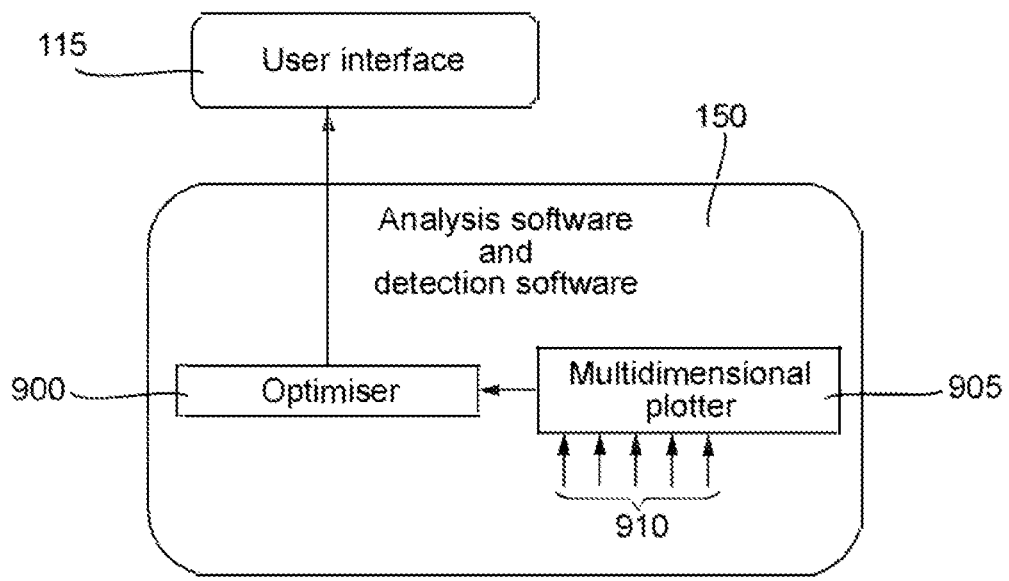
FIG. 9 shows components of an analyser for use in the detector assembly of FIG. 1.

Referring to FIG. 9, the analyser 150 of the materials classifier comprises software running on a digital processor. Broadly, the classifying analyser 150 is configured to analyze relationships between detected radiation events in different detected energy bands, the analysis being carried out for each of a number of different materials or material types for the purpose of identifying clusters in the results that are sufficiently distinguished to use for classifying the materials. The analyser 150 is configured to select one or more preferred relationships for distinguishing between the at least two different materials or material types.

The cluster analyser 150 receives channelized data 910 from the multichannel analyser 165 for each sample. These channels are usually quite narrow in energy range and evenly spaced along the energy spectrum detectable by means of the detector 170. This data is processed by a multidimensional plotter 905 for plotting relationships between detected events for different materials or material types, in relation to axes which each represent count values for detection events arising in a respective energy band. In FIG. 11, these energy bands are those relating to peaks in the data of FIG. 10.

The multidimensional plotter can be configured to combine data relating to different energy bands, or axes, for each sample in any of a range of different ways. Thus the data can be combined from different channels so as to create narrow or broad energy bands to which the data relates. Importantly, data can be used from one channel in more than one energy band. This can be seen in FIG. 10 where the energy band a5 quite clearly overlaps, and in this case contains, the energy bands a2 and a3. This data, whether sourced from individual energy bands or overlapping ones, can then be plotted on a variety of different axes from which an optimizer 900 component of the analyser 150 can select a preferred relationship for distinguishing between at least two different materials or material types. The preferred relationship will usually be a relationship that generates the most distinguishable clusters of results for the different materials or material types.

Figure 10:
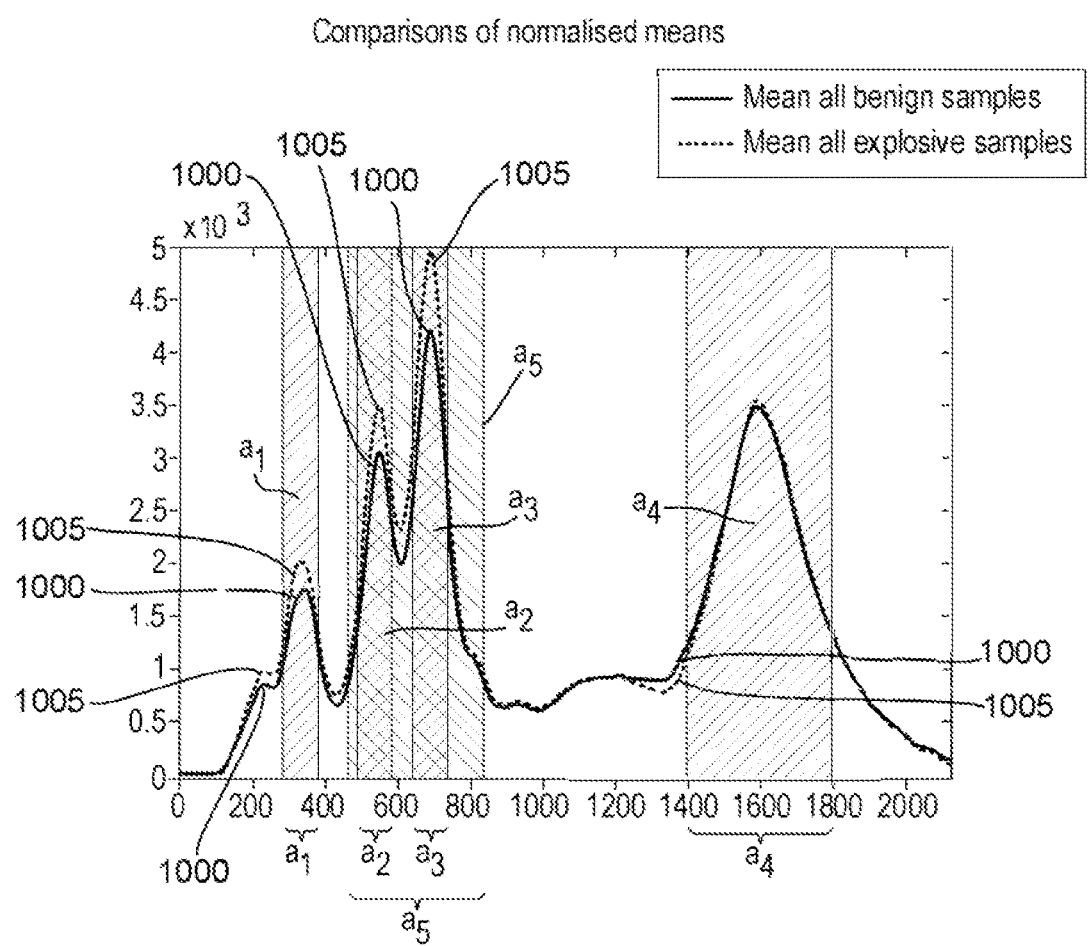
FIG. 10 shows a plot of the mean spectral responses of a number of explosive samples and a number of benign samples.
Figure 11:
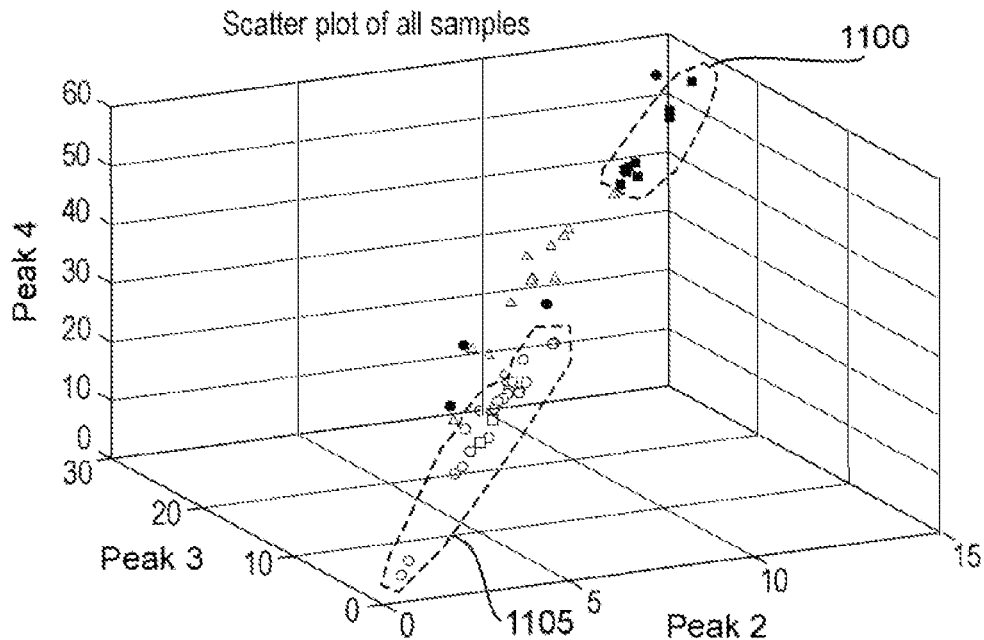
FIG. 11 shows a scatter plot of results obtained from a range of different material types.

Referring to FIG. 10, useful information in potentially classifying materials is available from a plot of the detected radiation arising in different energy bands. FIG. 10 shows the mean spectral signature responses 1000, 1005 from benign and explosive materials. Also shown is a number of spectral bands $a_1$ to $a_5$, in this example five. The bands in this case are selected to align with distinct known energy spectral features of the system. The bands could, however, also be selected at random, or for each band to cover an adjacent slot in a spectrum such that the entire spectrum is represented as a set of bands.

The five spectral bands shown in FIG. 10 represent pertinent features of the gamma backscatter spectrum that correspond to known energy lines of the backscattered gamma radiation from objects illuminated by a gamma source array containing a number of both Americium-241 and Barium-133 sources. Other sources and combination of sources may be used. Sources are typically selected to occupy different regions of the energy spectrum.

In the following, "a.u." represents an arbitrary unit. Each 'arbitrary unit' here is approximately 0.1 keV of energy, but the scale is not absolutely calibrated.

The spectral feature lying at the energy of ~3600 a.u., not shown, is often used as a reference spectral peak for the calibration of the energy scale (x-axis) and the intensity scale (y-axis). This compensates for drift in the spectral energies (a consequence of thermal effects in the detector) and also compensates for variation in spectral intensity (resulting from different spectrum integration times, distance between object and detector, attenuating materials). The above spectra are calibrated using these features. Calibration of the energy axis (x-axis) is required for consistency between measurements, although calibration of the intensity (y-axis) may not be necessary as this could be later corrected for in the later normalisation of the spectral signature data array. Each of the spectral bands shown in the above figure represents a range of energy, not necessarily of equal width, over which the total number of detected photon counts is summed, or equivalently integrated if the spectrum is continuous. In the example shown, a total of five bands have been used. The sum of the counts under each of these five bands can be represented as a data array of length five (in this case), such that:

$$a_n = \begin{bmatrix} a_1 \\ a_2 \\ a_3 \\ a_4 \\ a_5 \end{bmatrix}$$

where n is the identifier for a material or sample.

The array, in this case of length five, can be represented as a point in five-dimensional data space. A data matrix of multiple, m, samples of different types can be constructed; each spectral sample as a member of the set $\{n_1, n_2, \ldots, n_m\}$ resulting in a data matrix $A = [a_{n_1}, a_{n_2} \ldots a_{n_m}]$.

FIG. 11 shows an example of s scatter plot, where each point represents a different sample material, here represented in only three of three five available dimensions. The dimensions (axes) in this example represent the data counts under peaks 2, 3, and 4, relating to energy bands $a_2$ to $a_4$.

Figure 12:
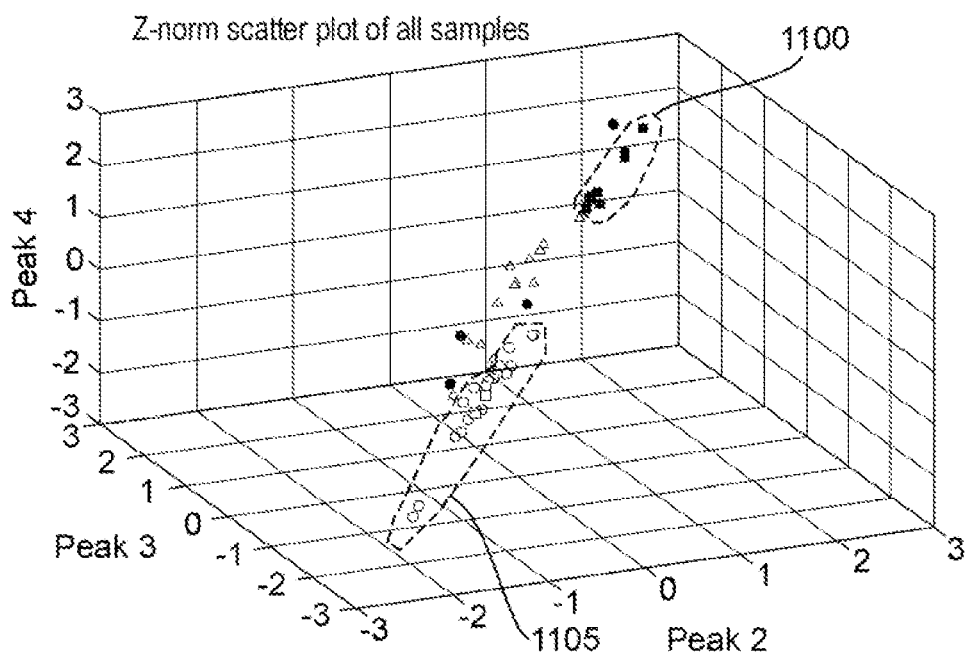
FIG. 12 shows the scatter plot of FIG. 11 after normalization.

The data array can be normalised in one of several standard ways. FIG. 12 shows the data normalised using the z-normalisation method $$\left(z_{norm} = \frac{x - \bar{x}}{\sigma_X}\right).$$

In FIGS. 11 and 12, the scatter points indicate a broad category (class) of each sample. For example, as listed on the figures, the upper points ringed by dotted lines 1100 represent explosives contained within electrical devices and the lower points ringed by dotted lines 1105 represent explosives in glass containers (together with a couple of simulants not distinguished here).

Figure 13:
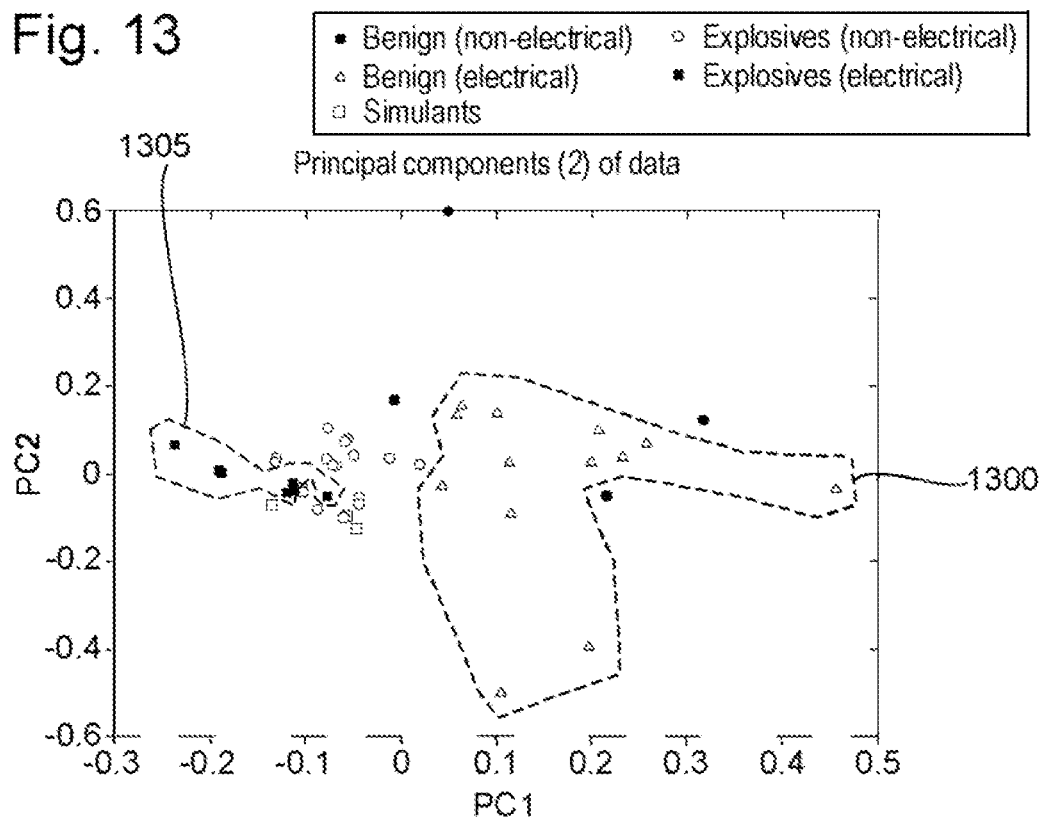
FIG. 13 shows the data of FIG. 12 after principal component analysis.
Figure 14:
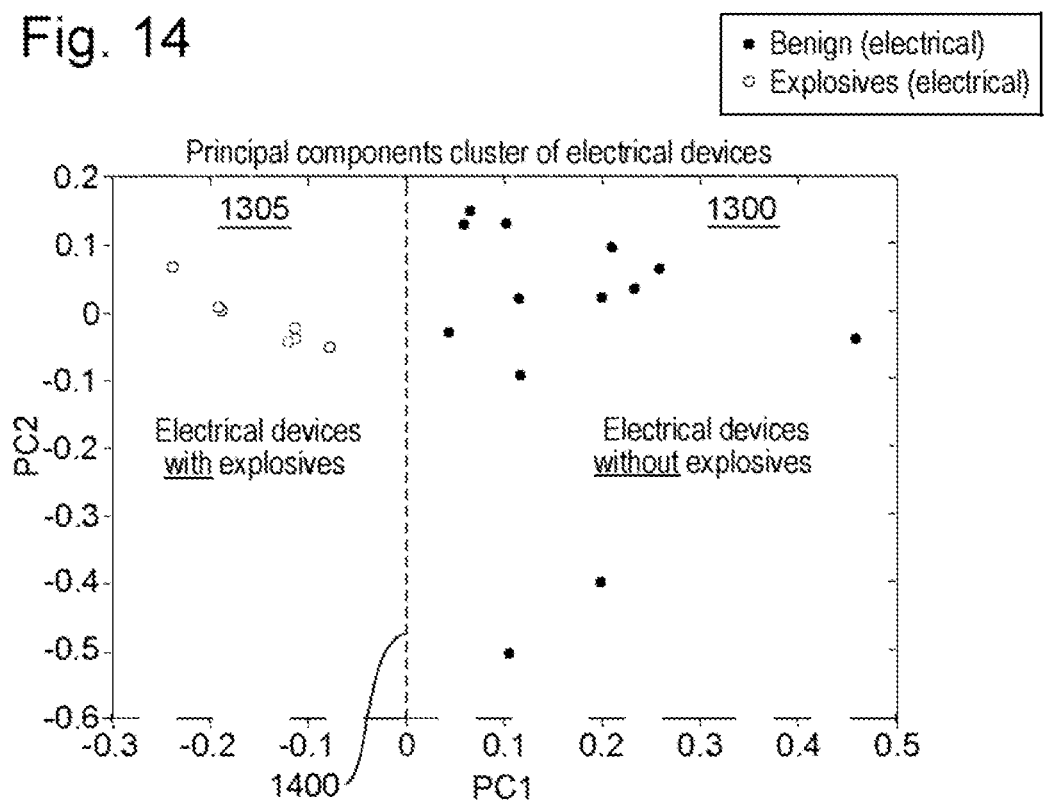
FIG. 14 shows data for two separable clusters from FIG. 13.

The aggregate data set contains strong variance along one dimension of the data, where this dimension is a compound of several axes. The standard technique for normalising such data is to use principal components analysis that transforms the data to a new set of axes aligned with the orthogonal axes of most variance. Realignment of data to the principal components, and representing only the first two (most significant) components of this data, is shown in FIG. 13 which represents two of the axes of the transformed data. In this case, the two sets of data selected relate to points shown to the right, ringed by dotted lines 1300 representing benign material contained within electrical devices, and points to the left ringed by dotted lines 1305 representing explosives contained within electrical devices The representation of the data in this manner demonstrates that a classifier can then be used that separates clusters representing materials of different categories. For example, FIG. 14 shows a subset of the data shown in FIG. 13, comprising the same data 1305, 1300, for electrical devices both with and without explosive materials contained within. This data can be seen to be clearly separated either side of the dotted line 1400.

Embodiments of the invention can be used in generating a reference tool and also then in identifying a category for materials of unknown type. The reference tool in this case will be a body of previously assembled and categorised data obtained as output of the materials classifier with known materials. Identification of a material of unknown type is carried out by using the materials classifier or equivalent equipment for illumination of a sample with gamma radiation, detecting values for the responses of the material in a range of configurable energy bands and assigning the unknown material to a category, for example containing explosives or not containing explosives, on the basis of mapping those detected responses to the reference tool.

The invention claimed is:

1. A materials classifier for use in detecting the presence of at least one material or material type in a sample under test, the materials classifier comprising:
    a gamma radiation source holder for holding at least one gamma radiation source for irradiating a sample test location;
    a detector for detecting radiation events in a backscatter direction from the sample test location, the radiation events lying in at least three different detected energy bands; and
    a classifying analyser for analyzing two or more relationships between detected radiation events in the at least three different detected energy bands, the analysis being carried out for multiple different materials or material types,
    the classifying analyser being configured to combine two or more of the detected radiation events into a first cluster of radiation events within a first one of the at least three different detected energy bands and to combine two or more of the detected radiation events into a second cluster of radiation events within a second one of the at least three different detected energy bands,
    the classifying analyser being configured to compare count values for each of the detected radiation events lying in the first cluster of radiation events against count values for each of the detected radiation events lying in the second cluster of radiation events, the classifying analyser being configured to select one or more preferred relationships for distinguishing between the different materials or material types based on the comparison.

2. The materials classifier according to claim 1, wherein the classifying analyser is configured to compare the count values to determine peaks in the first cluster of radiation events and in the second cluster of radiation events, wherein the first one of the at least three different detected energy bands relates to the peaks in the first cluster of radiation events, and wherein the second one of the at least three different detected energy bands relates to the peaks in the second cluster of radiation events.

3. The materials classifier according to claim 1, wherein the classifying analyser comprises a multidimensional plotter for plotting relationships between count values for detected events for different materials or material types, in relation to axes which each represent count values arising in a respective energy band.

4. The materials classifier according to claim 1, wherein the classifying analyser is configured to select a preferred relationship for distinguishing between the at least two different materials or material types.

5. The materials classifier according to claim 1, wherein the at least three different detected energy bands on which relationships are based are not mutually exclusive, two or more of these detected energy bands showing spectral overlap.

6. The materials classifier according to claim 1, wherein the detector is further provided with a multichannel analyser configured to provide a channelized output to the classifying analyser, each channel relating to detected energy events in a respective detected energy band, the classifying analyser being configured to combine output from more than one channel to generate data for plotting a relationship.

7. The materials classifier according to claim 6, wherein two or more of the detected energy bands on which a relationship is based show spectral overlap, the output from at least one channel of the multichannel analyser being used by the classifying analyser to generate data in relation to more than one detected energy band.

8. The materials classifier according to claim 1, wherein the classifying analyser is configured to use data clustering to select the one or more preferred relationships.

9. The materials classifier according to claim 1, being configured to output a record comprising a set of preferred relationships, based on results obtained with multiple different samples, for use in identifying unknown materials.

10. A materials identifier for identifying materials of unknown type, the materials identifier comprising:
a gamma radiation source holder for holding at least one gamma radiation source for irradiating a sample test location;
a detector for detecting radiation events in a backscatter direction from the sample test location, the events lying in at least two different detected energy bands; and
an analyser for compiling count values for the events arising in each energy band and comparing the count values with one or more of a set of relationships obtained by use of the materials classifier according to claim 9.

11. A method of classifying materials by means of their spectral response to gamma radiation, the method comprising;

irradiating multiple different samples with gamma radiation;
detecting radiation events in the backscatter direction, the radiation events lying in at least two detected energy bands;
sorting the detected radiation events into at least two detected_energy bands;
combining two or more of the detected radiation events into a first cluster of radiation events within a first one of the at least two detected energy bands and combining two or more of the detected radiation events into a second cluster of radiation events within a second one of the at least two detected energy bands;
comparing count values for each of the detected radiation events lying in the first cluster of radiation events against count values for each of the detected radiation events lying in the second cluster of radiation events; and
selecting a combination of the at least two detected energy bands to define at least one relationship that best distinguishes between clusters of spectral responses for different material classes based on the comparison.

12. The method according to claim 11, wherein at least two of the selected energy bands in the combination overlap.

13. A method of identifying a material, the method comprising:
irradiating the material with gamma radiation;
detecting a spectral response in the backscatter direction;
sorting the spectral response into energy bands; and
identifying the material by reference to at least one relationship obtained by the method of claim 11.

14. A system for use in detecting the presence of at least one material or material type in a sample under test, the system comprising:
a gamma radiation source holder for holding at least one gamma radiation source for irradiating a sample test location;
a detector for detecting radiation events in a backscatter direction from the sample test location, the events lying in at least three different detected energy bands; and
a classifying analyser for analyzing two or more relationships between detected radiation events in the at least three different detected energy bands, the analysis being carried out for multiple different materials or material types, the classifying analyser being configured to (1) to compare count values for detected events lying in respective ones of the at least three different energy bands, wherein two or more of the detected radiation events are combined into a first cluster of radiation events within a first one of the at least three different detected energy bands and two or more of the detected radiation events are combined into a second cluster of radiation events within a second one of the at least three different detected energy bands, and (2) select a preferred relationship for distinguishing between the at least two different materials or material types based on the comparison.

15. The system according to claim 14, wherein the classifying analyser comprises a multidimensional plotter for plotting relationships between count values for detected events for different materials or material types, in relation to axes which each represent count values arising in a respective energy band.

16. The system according to claim 14, wherein first and second bands of the at least three different detected energy bands overlap with one another.

17. The system according to claim 14, comprising a multichannel analyser configured to provide a channelized output to the classifying analyser, each of a first channel and a second channel relating to detected energy events in a respective detected energy band, the classifying analyser being configured to combine output from the first and second channels to generate data for analyzing a relationship, wherein two or more of the detected energy bands on which a relationship is based spectrally overlap.

18. The system according to claim 14, wherein the classifying analyser is configured to use data clustering to select the one or more preferred relationships.

19. The system according to claim 14, being configured to output a record comprising a set of preferred relationships, based on results obtained with multiple different samples, for use in identifying unknown materials.

20. The system according to claim 14, comprising a materials identifier for identifying materials of unknown type, the materials identifier including:
- a gamma radiation source holder for holding at least one gamma radiation source for irradiating a sample test location;
- a detector for detecting radiation events in a backscatter direction from the sample test location, the events lying in at least two different detected energy bands; and
- an analyser for compiling count values for the events arising in each energy band and comparing the count values with one or more relationships obtained by the classifying analyser.

* * * * *